(12) United States Patent
Tatami et al.

(10) Patent No.: US 10,585,505 B2
(45) Date of Patent: Mar. 10, 2020

(54) TRANSPARENT CONDUCTIVE FILM (71) Applicant: TOYOBO CO., LTD., Osaka-shi, Osaka (JP)

(72) Inventors: Naka Tatami, Otsu (JP); Yukihiro Numata, Otsu (JP)

(73) Assignee: TOYOBO CO., LTD., Osaka-shi (JP)

(*) Notice: Subject to any disclaimer, the term of this patent is extended or adjusted under 35 U.S.C. 154(b) by 66 days.

(21) Appl. No.: 15/562,960

(22) PCT Filed: Mar. 23, 2016

(86) PCT No.: PCT/JP2016/059171
§ 371 (c)(1),
(2) Date: Sep. 29, 2017

(87) PCT Pub. No.: WO2016/158606
PCT Pub. Date: Oct. 6, 2016

(65) Prior Publication Data
US 2018/0113526 A1 Apr. 26, 2018

(30) Foreign Application Priority Data

Mar. 31, 2015 (JP) .................. 2015-071243
Jan. 26, 2016 (JP) .................. 2016-012142

(51) Int. Cl.
*B32B 9/00* (2006.01)
*G06F 3/041* (2006.01)
(Continued)

(52) U.S. Cl.
CPC ............... *G06F 3/041* (2013.01); *B32B 9/00* (2013.01); *C08J 5/18* (2013.01); *C23C 14/08* (2013.01);
(Continued)

(58) Field of Classification Search
None
See application file for complete search history.

(56) References Cited

U.S. PATENT DOCUMENTS

| 5,225,273 A | 7/1993 | Mikoshiba et al. |
| 6,617,056 B1 * | 9/2003 | Hara .................. C23C 14/0036 204/192.14 |

(Continued)

FOREIGN PATENT DOCUMENTS

| EP | 1 591 554 A1 | 11/2005 |
| JP | 2001-226148 A | 8/2001 |

(Continued)

OTHER PUBLICATIONS

International Search Report dated May 31, 2016, issued in counterpart of International Application No. PCT/JP2016/059171 (1 page).

(Continued)

*Primary Examiner* — Seth Dumbris
*Assistant Examiner* — Kim S. Horger
(74) *Attorney, Agent, or Firm* — Westerman, Hattori, Daniels & Adrian, LLP (57) ABSTRACT

Provided is a transparent conductive film including a transparent plastic film substrate and an indium-tin composite oxide transparent conductive film laminated on at least one surface of the transparent plastic film substrate, a value of the normalized integrated intensity of a diffraction peak measured by X-ray diffractometry in the (222) plane due to a crystal of the transparent conductive film being 4 to 25 cps·°/nm.

4 Claims, 2 Drawing Sheets

(51) Int. Cl.
    *G01N 23/201*     (2018.01)
    *G01N 23/207*     (2018.01)
    *C23C 14/08*     (2006.01)
    *C08J 5/18*     (2006.01)
    *G06F 3/045*     (2006.01)
    *H01B 5/14*     (2006.01)

(52) U.S. Cl.
    CPC ......... *G01N 23/201* (2013.01); *G01N 23/207* (2013.01); *G06F 3/045* (2013.01); *H01B 5/14* (2013.01); *C23C 14/086* (2013.01)

(56) References Cited

U.S. PATENT DOCUMENTS

| | | | |
|---|---|---|---|
| 9,096,921 B2* | 8/2015 | Tatami | C23C 14/086 |
| 2003/0198808 A1 | 10/2003 | Muromachi et al. | |
| 2010/0232024 A1 | 9/2010 | Murota et al. | |
| 2015/0044361 A1 | 2/2015 | Subramanian et al. | |
| 2015/0118458 A1 | 4/2015 | Kobayashi et al. | |
| 2016/0239122 A1 | 8/2016 | Imamura et al. | |

FOREIGN PATENT DOCUMENTS

| | | |
|---|---|---|
| JP | 2004-71171 A | 3/2004 |
| JP | 2004071171 A * | 3/2004 |
| JP | 2012-107336 A | 6/2012 |
| JP | 5490955 B1 | 5/2014 |
| TW | 200808926 A | 2/2008 |
| TW | 201406664 A | 2/2014 |
| TW | 201506495 A | 2/2015 |

OTHER PUBLICATIONS

Extended (supplementary) European Search Report dated Sep. 4, 2018, issued in counterpart European Application No. 16772487.1 (8 pages).

Office Action dated Jul. 4, 2019, issued in counterpart TW Application No. 105109618, with English translation (7 pages).

Office Action dated Sep. 11, 2019, issued in counterpart EP application No. 16772487.1. (9 pages).

Park et al., "The effect of film microstructures on cracking of transparent conductive oxide (TCO) coatings on polymer substrates", Surface & Coatings Technology, Oct. 25, 2010, vol. 205, No. 3, pp. 915-921, cited in EP Office Action dated Sep. 11, 2019. (7 pages).

* cited by examiner

FIG. 1
(FIRST EXAMPLE)

FIG. 2
(SECOND EXAMPLE)

FIG. 3
(THIRD EXAMPLE)

FIG. 4
(FOURTH EXAMPLE)

FIG. 5

TRANSPARENT CONDUCTIVE FILM

TECHNICAL FIELD

The present invention relates to a transparent conductive film including a transparent plastic film substrate and a crystalline indium-tin composite oxide transparent conductive film laminated on the transparent plastic film substrate, particularly to a transparent conductive film excellent in pen sliding durability when used for a resistive film type touch panel and in flexibility.

BACKGROUND ART

A transparent conductive film including a transparent plastic substrate and a transparent and low resistance thin film laminated on the transparent plastic substrate has been widely used for application in electric and electronic fields, such as application of utilizing the electroconductivity of the film, e.g., a transparent electrode of, for example, flat panel displays such as a liquid crystal display and an electroluminescent (EL) display, and a touch panel.

A resistive film type touch panel includes in combination a fixed electrode obtained by coating a glass or plastic substrate with a transparent conductive thin film, and a movable electrode (film electrode) obtained by coating a plastic film with a transparent conductive thin film, and the resistive film type touch panel is used by overlapping thereof on an upper side of a display body. The film electrode is pressed with a finger or a pen, so that the fixed electrode and the transparent conductive thin film of the film electrode are brought into contact with each other to serve as an input for recognizing a position on the touch panel. In many cases, a pen applies stronger force on the touch panel than a finger. Successive input on the touch panel with a pen sometimes causes a rupture such as a crack or peeling on the transparent conductive thin film on the film electrode side. In addition, the transparent conductive thin film of the film electrode is sometimes broken at the time of bending the film electrode, for example, in a step of producing the touch panel or at the time of an input at an end portion of the touch panel. This breaking in the transparent conductive thin film is a phenomenon caused by insufficient flexibility of the transparent conductive thin film. In order to solve these problems, a transparent conductive film is required that attains both excellent pen sliding durability and flexibility.

A means for increasing the pen sliding durability includes a method of crystallizing the transparent conductive thin film on the film electrode side (for example, see PTD 1). In the conventional transparent conductive film, however, the crystallinity of an indium-tin composite oxide is controlled to realize a transparent conductive film excellent in pen sliding durability. The conventional transparent conductive film, however, has been insufficient when subjected to the flexibility test described below.

CITATION LIST

Patent Document

PTD 1: Japanese Patent Laying-Open No. 2004-071171

SUMMARY OF INVENTION

Technical Problems

An object of the present invention is to provide a transparent conductive film excellent in pen sliding durability when used for a touch panel and also in flexibility, in view of the conventional problem described above.

Solutions to Problems

The present invention has been achieved in view of the circumstances described above, and a transparent conductive film of the present invention that has been capable of solving the above problem is configured as follows.

1. A transparent conductive film including a transparent plastic film substrate and an indium-tin composite oxide transparent conductive film laminated on at least one surface of the transparent plastic film substrate, a value of normalized integrated intensity of a diffraction peak measured by X-ray diffractometry in a (222) plane due to a crystal of the transparent conductive film being 4 to 25 cps·°/nm.

2. The transparent conductive film according to 1, wherein the indium-tin composite oxide transparent conductive film has a crystal grain size of 10 to 1000 nm.

3. The transparent conductive film according to 1 or 2, wherein the indium-tin composite oxide transparent conductive film includes 0.5 to 10% by mass of tin oxide.

4. The transparent conductive film according to any one of 1 to 3, wherein the indium-tin composite oxide transparent conductive film has a thickness of 10 to 30 nm.

Advantageous Effects of Invention

The present invention can provide a transparent conductive film that has excellent pen sliding durability and flexibility in combination. A resultant transparent conductive film is very useful for application such as a resistive film type touch panel.

DESCRIPTION OF EMBODIMENT

A transparent conductive film of the present invention includes a transparent plastic film substrate and an indium-tin composite oxide transparent conductive film laminated on at least one surface of the transparent plastic film substrate, a value of the normalized integrated intensity of a diffraction peak measured by X-ray diffractometry in the (222) plane due to a crystal of the transparent conductive film being preferably 4 to 25 cps·°/nm.

The value of the normalized integrated intensity of a diffraction peak observed by X-ray diffractometry in the (222) plane indicates the degree of crystallinity of the indium-tin composite oxide transparent conductive film. The larger the value of the normalized integrated intensity of a diffraction peak is, the higher the crystallinity of the indium-tin composite oxide transparent conductive film is. Generally, the indium-tin composite oxide transparent conductive film high in crystallinity is hard, so that the transparent conductive film is excellent in pen sliding durability but inferior in flexibility. In the transparent conductive film of the present invention, the crystallinity is appropriately controlled to give a semi crystalline state described below, thereby allowing the transparent conductive film to have excellent pen sliding durability and flexibility in combination.

Here, the X-ray diffractometry is described.

When a diffraction peak from an indium-tin composite oxide transparent conductive film laminated on a transparent plastic film is measured, it is often difficult to perform accurate measurement with a concentration method optical system because of strong diffraction from the transparent plastic film. In many cases, the concentration method optical system can be used for measurement when the transparent conductive film is high in crystallinity, for example. The transparent conductive film of Patent Literature 1 can be measured with the concentration method optical system and is therefore high in crystallinity. As regards the transparent conductive film of the present invention, it is difficult to observe a diffraction peak in the (222) plane with the concentration method optical system. Therefore, a thin film method is used that is a measuring method of allowing the X-ray to be incident with a very shallow angle to the surface of a sample for restriction of penetration depth of the X-ray, to suppress as much influence as possible from the transparent plastic film.

The value of the normalized integrated intensity of a diffraction peak in the (222) plane due to a crystal of the indium-tin composite oxide transparent conductive film in the present invention is preferably greater than or equal to 4 cps·°/nm, more preferably greater than or equal to 7 cps·°/nm. With the value of the normalized integrated intensity greater than or equal to 4 cps·°/nm, the crystallinity for the pen sliding durability is preferably not insufficient. On the other hand, the value of the normalized integrated intensity of a diffraction peak in the (222) plane due to a crystal of the indium-tin composite oxide transparent conductive film is preferably less than or equal to 25 cps·°/nm, more preferably less than or equal to 23 cps·°/nm. With the value of the normalized integrated intensity less than or equal to 25 cps·° nm, the crystallinity does not excessively increase, so that the flexibility is preferably retained.

The indium-tin composite oxide transparent conductive film of the present invention preferably has a crystal grain size of greater than or equal to 10 nm. The crystal grain size is more preferably greater than or equal to 30 nm. With the crystal grain size greater than or equal to 10 nm, the bonding power between crystal grains is retained to preferably easily satisfy the pen sliding durability. On the other hand, the indium-tin composite oxide transparent conductive film preferably has a crystal grain size of less than or equal to 1000 nm. The crystal grain size is more preferably less than or equal to 500 nm. With the crystal grain size less than or equal to 1000 nm, the flexibility is preferably retained.

The transparent conductive film of the present invention includes an indium-tin composite oxide and preferably includes tin oxide in an amount of greater than or equal to 0.5% by mass and less than or equal to 10% by mass. Tin oxide in the indium-tin composite oxide is an impurity for indium oxide. The impurity tin oxide is contained to raise the melting point of the indium-tin composite oxide. That is, inclusion of the impurity tin oxide serves to inhibit crystallization. Inclusion of tin oxide in an amount of greater than or equal to 0.5% by mass preferably brings the surface resistance of the transparent conductive film up to a practical level. The content rate of tin oxide is further preferably greater than or equal to 1% by mass, particularly preferably greater than or equal to 2% by mass. With the content rate of tin oxide less than or equal to 10% by mass, the crystallization in adjustment to form the semi crystalline state described below easily occurs to preferably improve the pen sliding durability. The content rate of tin oxide is more preferably less than or equal to 8% by mass, further preferably less than or equal to 6% by mass, particularly preferably less than or equal to 4% by mass. The transparent conductive film of the present invention preferably has a surface resistance of 50 to 900 Ω/□.

In the present invention, the transparent conductive film desirably has a thickness of greater than or equal to 10 nm and less than or equal to 30 nm. The transparent conductive film having a thickness of greater than or equal to 10 nm is not excessively amorphous and thus easily gives appropriate crystallinity for forming the semi crystalline state described below, so that the pen sliding durability is preferably retained, consequently. The thickness of the transparent conductive film is more preferably greater than or equal to 13 nm, more preferably greater than or equal to 16 nm. On the other hand, the transparent conductive film having a thickness of less than or equal to 30 nm is not excessively crystalline and thus easily keep the semi crystalline state, so that the flexibility is preferably retained. The thickness of the transparent conductive film is more preferably less than or equal to 26 nm, further preferably less than or equal to 22 nm.

A production method for obtaining the transparent conductive film of the present invention is not particularly limited. The production method, however, can be exemplified as described below.

Figure 1:
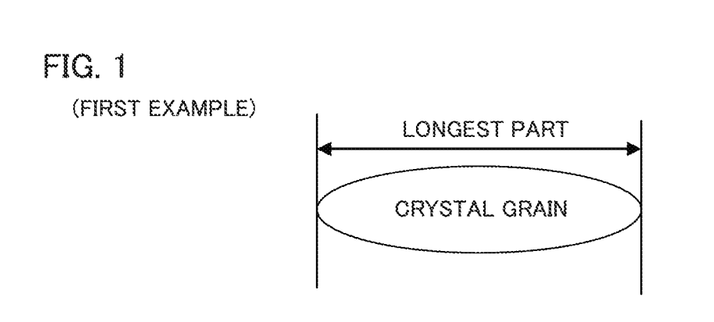
FIG. 1 is a schematic view illustrating one example (first example) of the longest part of a crystal grain in the present invention.
Figure 2:
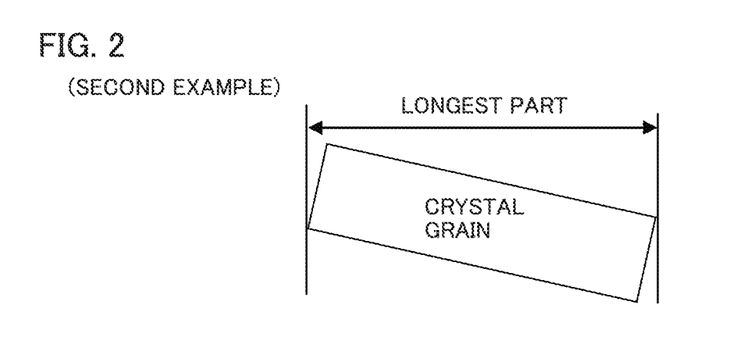
FIG. 2 is a schematic view illustrating another example (second example) of the longest part of a crystal grain in the present invention.
Figure 3:
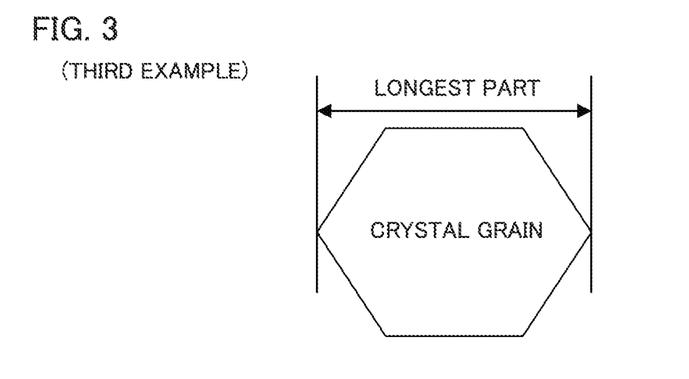
FIG. 3 is a schematic view illustrating another example (third example) of the longest part of a crystal grain in the present invention.
Figure 4:
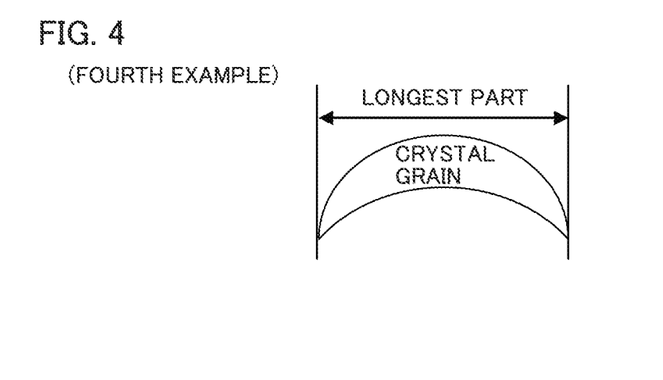
FIG. 4 is a schematic view illustrating another example (fourth example) of the longest part of a crystal grain in the present invention.
Figure 5:
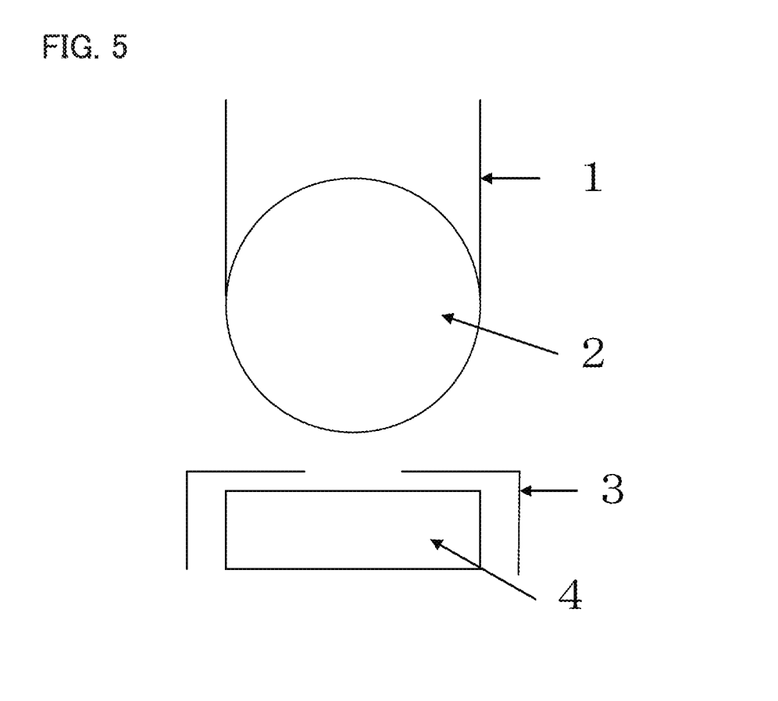
FIG. 5 is a schematic view for illustrating a position of a center roll in one example of a sputtering device suitably used in the present invention.

A sputtering method is preferably used as a method of forming the crystalline indium-tin composite oxide transparent conductive film on at least one surface of the transparent plastic film substrate. It is desirable to form the transparent conductive film on the transparent plastic film by accurately controlling the ratio of the partial pressure of water to the partial pressure of an inert gas in an atmosphere during sputtering so that the difference between the maximum value and the minimum value from the start to the completion of film formation becomes less than or equal to $2.0 \times 10^{-4}$, and by keeping the temperature of the film less than or equal to 80° C. during film formation. The temperature of the film during film formation is adjusted by using a setting temperature of a temperature controller for adjusting the temperature of a center roll in contact with the film that runs. Here, FIG. 5 illustrates a schematic view of one example of a sputtering device suitably used in the present invention, and a film 1 that runs is running partially in contact with the surface of a center roll 2. A chimney 3 is installed between an indium-tin sputtering target 4 and the film 1, and a thin film of indium-tin composite oxide is deposited and laminated on the surface of the film 1 traveling on the center roll 2. The temperature of center roll 2 is controlled by the temperature controller (not illustrated). Examples of the inert gas include helium, neon, argon, krypton, and xenon. The central value (the intermediate value between the maximum value and the minimum value) in the ratio of the partial pressure of water to the partial pressure of the inert gas in the atmosphere during sputtering is desirably $4.0 \times 10^{-4}$ to $2.9 \times 10^{-3}$. The central value in the ratio of the partial pressure of water to the partial pressure of the inert gas somewhat depends on the content rate of tin oxide in the indium-tin composite oxide transparent conductive film and the thickness of the transparent conductive film. When the amount of tin oxide added to the indium-tin composite oxide transparent conductive film is large or when the transparent conductive film is thin, it is desirable that the central value in the ratio of the partial pressure of water to the partial pressure of the inert gas be set low in the range described above. Contrarily, when the content rate of tin oxide in the indium-tin composite oxide transparent conductive film is low or when the transparent conductive film is thick, it is desirable that the central value in the ratio of the partial pressure of water to the partial pressure of the inert gas be set high in the range described above. In addition, it is desirable to add an oxygen gas during sputtering in order to bring the surface resistance and total light transmittance of the transparent conductive film up to a practical level.

The atmosphere for film formation largely including water is known to decrease the crystallinity of the transparent conductive film. Therefore, the amount of water in the atmosphere for film formation is an important factor. For control of the amount of water when the indium-tin composite oxide is formed into a film on the plastic film, it is desirable to actually observe the amount of water during film formation. It is not preferable to use an ultimate vacuum for the control of the amount of water in the atmosphere for film formation because of the following two reasons.

First, one of the reasons is that when the film is formed on the plastic film by sputtering, the film is heated to discharge moisture from the film, increasing the amount of water in the atmosphere for film formation to increase the amount of water compared with when the ultimate vacuum has been measured.

The second reason is applied to a case of a device that loads the transparent plastic film in large amounts. Such a device loads the film in a form of a film roll. A roll of film loaded into a vacuum chamber easily dehydrates on the outer layer portion of the roll, but is less likely to dehydrate on the inner layer portion of the roll. When the ultimate vacuum is measured, the plastic film roll is stopped, but since the film roll runs during thin film formation and the inner layer portion of the plastic film roll containing a large amount of water is unwound, the amount of moisture in the atmosphere during sputtering increases, and it increases more than the amount of moisture when the ultimate vacuum is measured. In the present invention, it is possible to preferably control the amount of water in the atmosphere during sputtering by observing the ratio of the partial pressure of water to the partial pressure of the inert gas in the atmosphere during sputtering.

The crystallinity of the transparent conductive film in the present invention is neither excessively high nor low (such crystallinity is referred to as semi crystallinity or a semi crystalline property). It is very difficult to stably make the transparent conductive film semi crystalline. This is because the semi crystallinity is a state where crystallization is stopped in middle of rapid phase transition from amorphousness to crystallinity. Therefore, the process is very sensitive to the amount of water in the atmosphere for film formation as a parameter involving the crystallinity, forming almost complete crystallinity (high crystallinity) when the amount of water is even slightly short in the atmosphere for film formation and contrarily forming amorphousness (low crystallinity) when the amount of water is even slightly excessive in the atmosphere for film formation. Thus, in the present invention, it is desirable to accurately control the ratio of the partial pressure of water to the partial pressure of the inert gas in the atmosphere during sputtering so that the difference between the maximum value and the minimum value from the start to the completion of film formation becomes less than or equal to $2.0 \times 10^{-4}$ in the method of forming the indium-tin composite oxide transparent conductive film on at least one surface of the transparent plastic film substrate. With the difference less than or equal to $2.0 \times 10^{-4}$ between the maximum value and the minimum value in the ratio of the partial pressure of water to the partial pressure of the inert gas in the atmosphere during sputtering, the transparent conductive film is less likely to be formed to have a mixture of a portion high in crystallinity and a portion low in crystallinity and easily becomes a transparent conductive film having uniform semi crystallinity, so that it is possible to suitably give the transparent conductive film that has excellent pen sliding durability and flexibility in combination.

As a method of accurately controlling the ratio of the partial pressure of water to the partial pressure of the inert gas in the atmosphere during sputtering so that the difference between the maximum value and the minimum value from the start to the completion of film formation becomes less than or equal to $2.0 \times 10^{-4}$, the following methods [1], [2], and [3] can be preferably employed, for example.

[1] Preferably employed is a method of introducing water into the atmosphere for film formation by a mass flow controller, continuously observing by a gas analyzer the ratio of the partial pressure of water to the partial pressure of the inert gas in the atmosphere during sputtering, and feeding back the observation result of the partial pressure of water to the mass flow controller, to accurately control the ratio of the partial pressure of water to the partial pressure of the inert gas in the atmosphere during sputtering so that the difference between the maximum value and the minimum value in the ratio becomes less than or equal to $2.0 \times 10^{-4}$.

[2] Preferably employed is a method of introducing a hydrogen atom-containing gas (such as hydrogen, ammonia, or a mixed gas of hydrogen and argon, this is not particularly limited as long as the gas contains a hydrogen atom) into the atmosphere for film formation by a mass flow controller, continuously observing by a gas analyzer the ratio of the partial pressure of water to the partial pressure of the inert gas in the atmosphere during sputtering, and feeding back the observation result of the partial pressure of water to the mass flow controller, to accurately control the ratio of the partial pressure of water to the partial pressure of the inert gas in the atmosphere during sputtering so that the difference between the maximum value and the minimum value in the ratio becomes less than or equal to $2.0 \times 10^{-4}$. The hydrogen atom-containing gas is separated in the atmosphere during sputtering to bond with, for example, oxygen in the atmosphere for film formation to form water. Therefore, the addition of the hydrogen atom-containing gas has an equivalent effect to the addition of water.

[3] It is desirable that the ratio of the partial pressure of water to the partial pressure of the inert gas in the atmosphere during sputtering be always observed by a gas analyzer and the observation result of the partial pressure of water be fed back to the temperature of the center roll in contact with the transparent plastic film, to accurately control the ratio of the partial pressure of water to the partial pressure of the inert gas in the atmosphere during sputtering so that the difference between the maximum value and the minimum value in the ratio becomes less than or equal to $2.0 \times 10^{-4}$. The transparent plastic film includes water, and therefore the amount of water discharged from the transparent plastic film can be controlled by changing the temperature applied to the transparent plastic film. For example, the temperature of the center roll in contact with the transparent plastic film may be increased for increasing the ratio of the partial pressure of water to the partial pressure of the inert gas in the atmosphere during sputtering. Contrarily, the temperature of the center roll in contact with the transparent plastic film may be decreased for decreasing the ratio of the partial pressure of water to the partial pressure of the inert gas in the atmosphere during sputtering. The temperature of the transparent plastic film is controlled by using the temperature of a heating medium in the temperature controller that controls the temperature of the center roll in contact with the transparent plastic film. In order to control the ratio of the partial pressure of water to the partial pressure of the inert gas in the atmosphere during sputtering, it is desirable to use a temperature controller whose response speed to temperature is high.

As the method of accurately controlling the ratio of the partial pressure of water to the partial pressure of the inert gas in the atmosphere during sputtering so that the difference between the maximum value and the minimum value from the start to the completion of film formation becomes less than or equal to $2.0 \times 10^{-4}$, the methods [1], [2], and [3] above are preferable for the following reasons.

In order to produce the transparent conductive film in high productivity, it is preferable to use the so-called roll type sputtering device that supplies a film roll and rolls up the film in a form of a film roll after formation of a film. In order to improve the productivity, a film roll of a long transparent plastic film is set in the roll type sputtering device. In a step of forming the transparent conductive film by a sputtering method, the film roll easily dehydrates on the outer layer portion but is less likely to dehydrate on the inner layer portion when the device inside is made into a substantially vacuum state. Directly after the start of sputtering, the outer layer portion of the film roll is fed, and the amount of water discharged from the film fed is small, so that the amount of water discharged into the atmosphere for film formation is small. As the sputtering continues, the film is continuously fed from the film roll for running sequentially from the outer layer to the inner layer to feed the inner layer portion of the film roll that includes more water, increasing the amount of water in the atmosphere for film formation. In addition, the film is often different in water content in the length-wise direction. In order to stably make the transparent conductive film semi crystalline, it is preferable to always monitor the amount of water and adjust the amount of water to an intended amount in prompt response to a detected change in the amount of water, because the amount of water in the atmosphere for film formation changes every moment. In the methods [1] and [2], the mass flow controller is used, and therefore it is possible to adjust the amount of water to an intended amount in prompt response to a detected change in the amount of water. In the method [3], the temperature controller high in response speed to temperature is used, and therefore it is possible to adjust the amount of water to an intended amount in prompt response to a detected change in the amount of water.

In the method of forming the crystalline indium-tin composite oxide transparent conductive film on at least one surface of the transparent plastic film substrate, it is desirable to form the transparent conductive film on the transparent plastic film by keeping the temperature of the film during sputtering less than or equal to 80° C. The film having a temperature of less than or equal to 80° C. prevents generation of a large amount of water and an impurity gas such as an organic gas from the film to desirably eliminate the possibility of a failure that the film slips with respect to the center roll.

In the method of forming the crystalline indium-tin composite oxide transparent conductive film on at least one surface of the transparent plastic film substrate, the central value in the ratio of the partial pressure of water to the partial pressure of the inert gas (the intermediate value between the maximum value and the minimum value from the start to the completion of film formation) in the atmosphere during sputtering is desirably $4.0 \times 10^{-4}$ to $3.0 \times 10^{-3}$. With the central value in the ratio of the partial pressure of water to the partial pressure of the inert gas greater than or equal to $4.0 \times 10^{-4}$, the crystallinity of the transparent conductive film does not excessively increase, so that the flexibility is preferably retained. With the central value in the ratio of the partial pressure of water to the partial pressure of the inert gas less than or equal to $3.0 \times 10^{-3}$, the crystallinity of the transparent conductive film does not excessively decrease, so that the pen sliding durability is preferably retained. The central value in the ratio of the partial pressure of water to the partial pressure of the inert gas also depends on the amount of tin oxide added to the indium-tin composite oxide transparent conductive film and the thickness of the transparent conductive film. When the amount of tin oxide added to the indium-tin composite oxide transparent conductive film is large or when the transparent conductive film is thin, it is desirable that the central value in the ratio of the partial pressure of water to the partial pressure of the inert gas be set low in the range described above. Contrarily, when the amount of tin oxide added to the indium-tin composite oxide transparent conductive film is low or when the transparent conductive film is thick, it is desirable that the central value in the ratio of the partial pressure of water to the partial pressure of the inert gas be set high in the range described above.

In the method of forming the crystalline indium-tin composite oxide transparent conductive film on at least one surface of the transparent plastic film substrate, it is desirable to introduce an oxygen gas during sputtering. The introduction of an oxygen gas during sputtering preferably eliminates a failure caused by a lack of oxygen in the indium-tin composite oxide transparent conductive film, lowers the surface resistance of the transparent conductive film, and increases the total light transmittance. Therefore, it is desirable to introduce an oxygen gas during sputtering in order to bring the surface resistance and total light transmittance of the transparent conductive film up to a practical level.

The transparent conductive film of the present invention preferably has a total light transmittance of 70 to 95%.

The transparent conductive film of the present invention is desirably formed through a heating treatment in an atmosphere including oxygen at 80 to 200° C. for 0.1 to 12 hours after the indium-tin composite oxide transparent conductive film is formed and laminated on the transparent plastic film substrate. With the temperature greater than or equal to 80° C., a treatment of slightly increasing the crystallinity for forming a semi crystalline state is easy to preferably increase the pen sliding durability. With the temperature less than or equal to 200° C., the flatness of the transparent plastic film is preferably secured.

<Transparent Plastic Film Substrate>

The transparent plastic film substrate used in the present invention is a film obtained by subjecting an organic polymer to melt extrusion or solution extrusion to form a film and subjecting the resultant film, as necessary, to drawing in the length-wise direction and/or the width-wise direction, cooling, and heat setting. Examples of the organic polymer include polyethylene, polypropylene, polyethylene terephthalate, polyethylene-2,6-naphthalate, polypropylene terephthalate, nylon 6, nylon 4, nylon 66, nylon 12, a polyimide, a polyamide-imide, polyethersulfone, polyetheretherketone, polycarbonate, polyarylate, cellulose propionate, polyvinyl chloride, polyvinylidene chloride, polyvinyl alcohol, polyether imide, polyphenylene sulfide, polyphenylene oxide, polystyrene, syndiotactic polystyrene, and a norbornene polymer.

Among these organic polymers, preferred are, for example, polyethylene terephthalate, polypropylene terephthalate, polyethylene-2,6-naphthalate, syndiotactic polystyrene, a norbornene polymer, polycarbonate, and polyarylate. These organic polymers may be copolymerized with a monomer of another organic polymer in a small amount or blended with another organic polymer.

The transparent plastic film substrate used in the present invention has a thickness ranging preferably from 10 to 300 µm, particularly preferably from 70 to 260 µm. The plastic film having a thickness of greater than or equal to 10 µm is preferable from the viewpoint of durability because the mechanical strength is retained to be small in distortion against an input with a pen when the plastic film substrate is used particularly for a touch panel. On the other hand, the transparent plastic film substrate having a thickness of less than or equal to 300 µm is preferable because it is unnecessary to particularly increase a load for recognition of a position by an input with a pen when the transparent plastic film substrate is used for a touch panel.

The transparent plastic film substrate used in the present invention may be subjected to a surface activation treatment such as a corona discharge treatment, a glow discharge treatment, a flame treatment, an ultraviolet radiation treatment, an electron beam radiation treatment, or ozonation without impairing the purpose of the present invention.

An effect of increasing the pen sliding durability can be expected when the transparent plastic film substrate is coated with a curable resin layer a surface of which is made into projections and recesses and then the transparent conductive film is formed on the projections and recesses. The effect includes two main points. The first point is that the adhesion force between the transparent conductive thin film and the curable resin layer is increased to prevent peeling of the transparent conductive film caused by sliding of a pen, increasing the pen sliding durability. The second point is that an actual contact area decreases that is made when sliding of a pen brings the transparent conductive thin film into contact with glass, to improve the slidability between a glass surface and the transparent conductive film, increasing the pen sliding durability. The curable resin layer will be described in detail below.

<Curable Resin Layer>

The curable resin preferably used in the present invention is not particularly limited as long as it is a resin cured by application of energy such as heating, irradiation with ultraviolet, or irradiation with an electron beam, and examples of the curable resin include a silicone resin, an acrylic resin, a methacrylic resin, an epoxy resin, a melamine resin, a polyester resin, and a urethane resin. From the viewpoint of productivity, an ultraviolet curable resin is preferably contained as a main component.

Examples of such an ultraviolet curable resin can include polyfunctional acrylate resin such as acrylic acid (ester) or methacrylic acid ester of polyhydric alcohol; and polyfunctional urethane acrylate resins synthesized from diisocyanates, polyhydric alcohols, and hydroxyalkyl esters of acrylic acid or methacrylic acid. A monofunctional monomer such as vinylpyrrolidone, methylmethacrylate, or styrene can be added to these polyfunctional resins for copolymerization as necessary.

In order to increase the adhesion force between the transparent conductive thin film and the curable resin layer, it is effective to treat a surface of the curable resin layer by the following techniques. Specific examples of the techniques include a discharge treatment method of irradiating the surface by glow or corona discharge to increase a carbonyl group, a carboxyl group, and a hydroxyl group, and a chemical agent treatment method of treating the surface with an acid or an alkali to increase polar groups such as an amino group, a hydroxyl group, and a carbonyl group.

For the use of the ultraviolet curable resin, a photoinitiator is usually added. As the photoinitiator, a known compound that absorbs ultraviolet and generates a radical can be used without any particular limitation, and examples of such a photoinitiator include various benzoins, phenylketones, and benzophenones. It is preferable to usually set the amount of the photoinitiator added to the ultraviolet curable resin to 1 to 5 parts by mass per 100 parts by mass of the ultraviolet curable resin.

In the present invention, the curable resin layer preferably contains, in addition to the main constituent curable resin, a resin non-compatible with the curable resin in combination. The combination use of a small amount of resin non-compatible with the matrix curable resin can cause phase separation in the curable resin to disperse the non-compatible resin in a particle state. These dispersed particles of the non-compatible resin can form projections and recesses on a surface of the curable resin to increase the surface roughness in a wide region.

When the curable resin is the ultraviolet curable resin, examples of the non-compatible resin include a polyester resin, a polyolefin resin, a polystyrene resin, and a polyamide resin.

In the present invention, when the ultraviolet curable resin is used as the main constituent curable resin of the curable resin layer and a high molecular weight polyester resin is used as the polymer resin non-compatible with the curable resin, the polyester resin is blended in a ratio of preferably 0.1 to 20 parts by mass, further preferably 0.2 to 10 parts by mass, particularly preferably 0.5 to 5 parts by mass, to 100 parts by mass of the ultraviolet curable resin.

With the polyester resin having a blending amount of greater than or equal to 0.1 parts by mass per 100 parts by mass of the ultraviolet curable resin, the projections formed on the surface of the curable resin layer are not excessively small to effectively impart the surface roughness, preferably giving an effect of further improving the pen sliding durability. On the other hand, with the polyester resin having a blending amount of less than or equal to 20 parts by mass per 100 parts by mass of the ultraviolet curable resin, the curable resin layer preferably retains chemical resistance as well as strength.

The polyester resin, however, is sometimes less preferable because the difference in refractive index between the polyester resin and the ultraviolet curable resin tends to increase a haze value of the curable resin layer and decrease the transparency of the curable resin layer. The high molecular weight polyester resin can also preferably be used as an antiglare film having a high haze value and thus having an antiglare function by contrarily, in a positive manner, using the deterioration in transparency caused by dispersed particles of the polyester resin.

Each of the ultraviolet curable resin, the photoinitiator, and the high molecular weight polyester resin is dissolved in a common solvent to prepare a coating solution. The solvent used is not particularly limited, and examples of the solvent include alcohol solvents such as ethyl alcohol and isopropyl alcohol, ester solvents such as ethyl acetate and butyl acetate, ether solvents such as dibutyl ether and ethylene glycol monoethyl ether, ketone solvents such as methyl isobutyl ketone and cyclohexanone, and aromatic hydrocarbon solvents such as toluene, xylene, and solvent naphtha. These solvents can be used singly or in mixture.

The concentration of the resin components in the coating solution can be appropriately selected in consideration of, for example, viscosity suitable for a coating method. For example, the total amount of the ultraviolet curable resin, the photoinitiator, and the high molecular weight polyester resin usually accounts for 20 to 80% by mass of the coating solution. This coating solution may also contain, as necessary, other known additives such as a silicone leveling agent.

In the present invention, the transparent plastic film substrate is coated with the coating solution prepared. A coating method is not particularly limited, and a conventionally know method can be used, such as a bar coating method, a gravure coating method, or a reverse coating method.

The coating solution applied is subjected to a next drying step where the solvent is removed by evaporation. In this step, the high molecular weight polyester resin that has been uniformly dissolved in the coating solution is formed into fine particles and precipitated in the ultraviolet curable resin. The resultant coating layer is dried and the plastic film is irradiated with ultraviolet to cross-link and cure the ultraviolet curable resin to form the curable resin layer. In this curing step, the fine particles of the high molecular weight polyester resin are fixed into the hard coat layer and form protrusions on the surface of the curable resin layer to increase the surface roughness in a wide region.

The curable resin layer preferably has a thickness ranging from 0.1 to 15 µm. The thickness ranges more preferably from 0.5 to 10 µm, particularly preferably from 1 to 8 µm. With the curable resin layer having a thickness of greater than or equal to 0.1 µm, sufficient protrusions are preferably formed. On the other hand, with the curable resin layer having a thickness of less than or equal to 15 µm, the productivity is preferably good.

EXAMPLES

The present invention will be described in further detail below with reference to examples. Any part of the present invention, however, is not limited by these examples. Various measurement evaluations in the examples were performed by the following methods.

(1) Total Light Transmittance

The total light transmittance was measured with use of NDH-2000 manufactured by NIPPON DENSHOKU INDUSTRIES CO., LTD. in accordance with JIS-K7136.

(2) Surface Resistance Value

The measurement was performed by a four-terminal method in accordance with JIS-K7194. Used as a measurement device was Loresta AX MCP-T370 manufactured by Mitsubishi Chemical Analytech, Co., Ltd.

(3) Value of Normalized Integrated Intensity of Diffraction Peak in (222) Plane

As regards the transparent conductive film of the present invention, it was difficult to observe a diffraction peak in the (222) plane with a concentration method optical system. Therefore, a thin film method was used that was a measuring method of allowing the X-ray to be incident with a very shallow angle to the surface of a sample for restriction of penetration depth of the X-ray, to suppress as much influence as possible from the transparent plastic film.

The measurement was performed with use of the sample horizontally-holding X-ray diffractometer for thin film evaluation Smart Lab manufactured by Rigaku Corporation as an X-ray diffractometer. A parallel beam optical system including a multilayer film mirror was used and a CuKα ray (wavelength: 1.54186 angstroms) was used as a light source with an output of 40 kV and 30 mA. Used as an incidence-end slit system was a soller slit (5.00), an incident slit (0.2 mm), and a longitudinal control slit (10 mm), and used as a receiving-end slit was a parallel slit analyzer (PSA) (0.114 deg). A 20-mm square sample may be fixed to a stage with double sided tape or fixed by suction with use of a porous suction sample holder. The measurement was performed at an incident angle of the X-ray of 0.25°, with a scintillation counter detector scanned in an out-of-plane direction, and at a step interval of 0.02° and a measurement speed of 2.0°/min. A diffraction line from the (222) plane of an ITO film appears at a position of about 30.5° (2θ) as a peak when a CuKα ray is used. Background subtraction was performed according to the Sonneveld-Visser method (Sonneveld, E. J. & Visser, J. W., J. Appl. Cryst. 8, 1 (1975)) and the integrated intensity of a diffraction peak in the (222) plane was calculated. A value obtained by dividing the integrated intensity by the thickness of the transparent conductive film is defined as a value of the normalized integrated intensity of the diffraction peak in the (222) plane. The thickness of the transparent conductive film was obtained by the method described in "(5) Thickness of transparent conductive film (film thickness)" below.

(4) Crystal Grain Size

A film specimen obtained by laminating the transparent conductive thin film layer was cut out into a size of 1 mm×10 mm and attached to an upper surface of an appropriate resin block with the surface of the conductive thin film directed outside. After the film specimen was trimmed, an ultra-thin piece approximately parallel to the film surface was prepared by a general technical method of ultra microtome.

This piece was observed with a transmission electron microscope (JEM-2010 manufactured by JEOL Ltd.) to select a conductive thin film part that had no remarkable damage, and the part was photographed with a direct magnification of 40000 times by accelerating voltage of 200 kV.

All the crystal grains observed under the transmission electron microscope are measured for their longest parts and the average value of their measurement values is defined as a crystal grain size. Here, FIGS. 1 to 4 illustrate examples involving a method of identifying the longest part in the measurement of the maximum length of a crystal grain. That is, the longest part is identified by the length of a straight line that can be measured as the longest grain size of a crystal grain.

(5) Thickness of Transparent Conductive Film (Film Thickness)

A film specimen obtained by laminating the transparent conductive thin film layer was cut out into a size of 1 mm×10 mm and embedded in an epoxy resin for an electron microscope. The embedded specimen was fixed to a sample holder of an ultra microtome and a cross-sectional thin piece was prepared that is parallel with a short side of the specimen embedded. Next, this piece was photographed at a portion that had no remarkable damage of the thin film with a transmission electron microscope (JEM-2010 manufactured by JEOL Ltd.) at an accelerating voltage of 200 kV and an observation magnification of 10000 times in a bright field, and the film thickness was measured from the photograph obtained.

(6) Pen Sliding Durability Test

The transparent conductive film was used as one panel plate, and used as the other panel plate was a transparent conductive thin film (S500, manufactured by Nippon Soda Co., Ltd.) that included a glass substrate and a 20-nm thick indium-tin composite oxide thin film (tin oxide content: 10% by mass) laminated on the glass substrate by a plasma CVD method. These two panel plates were disposed so as to face their transparent conductive thin films with epoxy beads having a diameter of 30 μm interposed between the panel plates to prepare a touch panel. Next, the touch panel was subjected to a 150000 reciprocal linear sliding test with a load of 2.5 N applied to a polyacetal pen (tip shape: 0.8 mm R). In the test, the sliding distance was 30 mm and the sliding speed was 180 mm/s. After this sliding durability test, first, the sliding portion was visually observed to confirm whether or not it was whitened. Further, an ON-resistance (resistance value when a movable electrode (film electrode) was brought into contact with a fixed electrode) was measured with the sliding portion pressed with a pen load of 0.8 N. The ON-resistance is desirably less than or equal to 10 kΩ.

(7) Flexibility Test

The transparent conductive film was cut into a rectangular shape having a size of 20 mm×80 mm. Next, the rectangular-shaped transparent conductive film was measured for its resistance value with the short sides of the rectangle joined with a tester. The transparent conductive film was bent with its transparent conductive film directed outside, and the bending diameter of the transparent conductive film was recorded when the resistance value of the tester started to increase. The bending diameter is desirably less than or equal to 15.5 mm.

(8) Measurement of Content Rate of Tin Oxide in Transparent Conductive Film

A sample (about 15 cm$^2$) was cut out and put in a quartz conical flask, 20 ml of 6 mol/l hydrochloric acid was added to the flask, and the flask was sealed with a film to prevent volatilization of the acid. The flask was sometimes shaken at room temperature and left to stand for 9 days to dissolve the ITO layer. The remaining film was taken out and the hydrochloric acid having the ITO layer dissolved therein was used as a measurement solution. The content rates of In and Sn in the dissolution solution were measured by a calibration curve method with use of an inductively coupled plasma (ICP) emission analyzer (maker: Rigaku Corporation, model: CIROS-120 EOP). As a measurement wavelength for each element, a non-interference and highly sensitive wavelength was selected. As standard solutions, commercially available standard solutions of In and Sn were used after diluted.

Each of the transparent plastic film substrates used in the examples and comparative examples is a biaxially oriented transparent PET film having an easily adhering layer on both surfaces thereof (A4340, manufactured by TOYOBO CO., LTD., thickness 188 μm). As the curable resin layer, a coating solution was prepared by blending 3 parts by mass of a copolymer polyester resin (VYLON 200, manufactured by TOYOBO CO., LTD., weight average molecular weight 18,000) with 100 parts by mass of a photoinitiator-containing acrylic resin (SEIKABEAM (registered trade name) EXF-01J, manufactured by Dainichiseika Color & Chemicals Mfg. Co., Ltd.), adding, as a solvent, a mixed solvent of toluene/MEK (8/2: ratio by mass) so that the solid content concentration became 50% by mass, and stirring the resultant solution for uniform dissolution (this coating solution is hereinafter referred to as a coating solution A). The transparent plastic film substrate was coated with the prepared coating solution with a Meyer bar so that the thickness of a coating layer became 5 μm. The coating layer was dried at 80° C. for 1 minute and irradiated with ultraviolet (light quantity: 300 mJ/cm$^2$) by an ultraviolet radiation device (UB042-5AM-W model, manufactured by EYE GRAPHICS CO., LTD.) to cure the coating layer.

Examples 1 to 9

Each example level was carried out as described below under the conditions indicated in Table 1.

The film was loaded into a vacuum chamber and the chamber was vacuumed up to $1.5 \times 10^{-4}$ Pa. Next, after introduction of oxygen, argon was introduced as an inert gas to adjust the total pressure to 0.5 Pa.

Power was applied on a sintered indium-tin composite oxide target or a sintered indium oxide target not containing tin oxide at a power density of 2 W/cm$^2$ to form a transparent conductive film by a DC magnetron sputtering method. The film thickness was controlled by changing the speed of the film when the film passed over the target. The ratio of the partial pressure of water to the partial pressure of the inert gas in the atmosphere during sputtering was measured with use of a gas analyzer (Transpector XPR3, manufactured by INFICON Co., Ltd.). For the purpose of adjusting, in each example level, the ratio of the partial pressure of water to the partial pressure of the inert gas in the atmosphere during sputtering, adjustment was performed, as indicated in Table 1, for the introduction amount of water or hydrogen atom-containing gas and the temperature of the heating medium in the temperature controller that controlled the temperature of the center roll with which the film ran in contact. In the example levels that employed the above-described method [3] of finely accurately controlling the change in the ratio of the partial pressure of water to the partial pressure of the inert gas in the atmosphere during sputtering from the start to the completion of film formation, the temperature of the temperature controller was changeably controlled, and the temperature right in the middle between the maximum value and the minimum value of the temperature from the start to the completion of film formation was listed as the central value in Table 1.

The film obtained by forming and laminating the transparent conductive film was subjected to the heating treatment indicated in Table 1 and then to the measurement. Table 1 shows the measurement results.

Comparative Example 1 to 7

Transparent conductive films were prepared in the same manner as in Example 1 under the conditions indicated in Table 1 and evaluated. Table 1 shows the results.

TABLE 1

| | Method of controlling (partial pressure of water/partial pressure of argon) (*1) | Central value of (partial pressure of water/partial pressure of argon) | Difference between maximum value and minimum value in (partial pressure of water/partial pressure of argon) | Flow of oxygen/ flow of argon | Content of tin oxide in transparent conductive film (% by mass) | Central temperature of temperature controller (° C.) | Film thickness (nm) |
|---|---|---|---|---|---|---|---|
| Example 1 | [1] | $1.13 \times 10^{-3}$ | $0.5 \times 10^{-4}$ | 0.055 | 3 | −10 | 20 |
| Example 2 | [2] | $1.13 \times 10^{-3}$ | $0.6 \times 10^{-4}$ | 0.055 | 3 | −10 | 20 |
| Example 3 | [3] | $1.15 \times 10^{-3}$ | $0.6 \times 10^{-4}$ | 0.055 | 3 | 10 | 20 |
| Example 4 | [3] | $4.10 \times 10^{-4}$ | $1.0 \times 10^{-4}$ | 0.055 | 1 | 5 | 14 |
| Example 5 | [3] | $1.30 \times 10^{-3}$ | $1.0 \times 10^{-4}$ | 0.055 | 10 | 5 | 30 |
| Example 6 | [3] | $1.11 \times 10^{-3}$ | $0.2 \times 10^{-4}$ | 0.055 | 3 | −12 | 20 |
| Example 7 | [3] | $1.20 \times 10^{-3}$ | $1.8 \times 10^{-4}$ | 0.055 | 3 | 7 | 20 |
| Example 8 | [3] | $2.92 \times 10^{-3}$ | $1.9 \times 10^{-4}$ | 0.045 | 1 | 70 | 30 |
| Example 9 | [3] | $1.32 \times 10^{-3}$ | $1.9 \times 10^{-4}$ | 0.026 | 0.5 | 10 | 20 |
| Comparative Example 1 | [3] | $3.80 \times 10^{-4}$ | $0.5 \times 10^{-4}$ | 0.046 | 3 | −12 | 23 |
| Comparative Example 2 | [3] | $3.10 \times 10^{-3}$ | $1.9 \times 10^{-4}$ | 0.055 | 3 | −12 | 20 |
| Comparative Example 3 | [3] | $1.15 \times 10^{-3}$ | $0.6 \times 10^{-4}$ | 0.055 | 11 | −10 | 20 |
| Comparative Example 4 | [3] | $1.15 \times 10^{-3}$ | $0.8 \times 10^{-4}$ | 0.055 | 3 | 10 | 8 |
| Comparative Example 5 | None | $2.68 \times 10^{-3}$ | $6.0 \times 10^{-4}$ | 0.055 | 1 | −10 | 20 |
| Comparative Example 6 | [3] | $1.12 \times 10^{-3}$ | $0.8 \times 10^{-4}$ | 0.055 | 3 | 5 | 32 |
| Comparative Example 7 | [3] | $3.25 \times 10^{-4}$ | $0.8 \times 10^{-4}$ | 0.025 | 0 | −12 | 25 |

| | Conditions of heating treatment | Total light transmittance (%) | Surface resistance (Ω/□) | Value of normalized integrated intensity of diffraction peak in (222) plane (cps · °/nm) | Crystal grain size (nm) | Pen sliding durability test | Flexibility test (mm) |
|---|---|---|---|---|---|---|---|
| Example 1 | 165° C. 75 min | 87.5 | 576 | 15.32 | 230 | Transparent at sliding portion On-resistance 0.2 kΩ | 14.8 |
| Example 2 | 165° C. 75 min | 87.4 | 587 | 14.52 | 220 | Transparent at sliding portion On-resistance 0.2 kΩ | 14.8 |
| Example 3 | 165° C. 75 min | 87.3 | 609 | 11.91 | 50 | Transparent at sliding portion On-resistance 0.2 kΩ | 11.5 |
| Example 4 | 180° C. 75 min | 88.2 | 870 | 5.98 | 80 | Transparent at sliding portion On-resistance 0.2 kΩ | 12.0 |
| Example 5 | 150° C. 60 min | 86.7 | 450 | 13.24 | 70 | Transparent at sliding portion On-resistance 0.2 kΩ | 15.4 |
| Example 6 | 165° C. 75 min | 87.6 | 653 | 22.81 | 110 | Transparent at sliding portion On-resistance 0.2 kΩ | 15.2 |
| Example 7 | 165° C. 75 min | 87.1 | 562 | 4.28 | 40 | Transparent at sliding portion On-resistance 0.2 kΩ | 10.7 |
| Example 8 | 165° C. 75 min | 85.9 | 720 | 4.02 | 30 | Transparent at sliding portion On-resistance 0.2 kΩ | 13.8 |
| Example 9 | 165° C. 75 min | 86.8 | 675 | 18.52 | 900 | Transparent at sliding portion On-resistance 0.2 kΩ | 15.2 |
| Comparative Example 1 | 150° C. 30 min | 87.4 | 528 | 27.62 | 200 | Transparent at sliding portion On-resistance 0.2 kΩ | 16.0 |
| Comparative Example 2 | 165° C. 75 min | 86.3 | 620 | 0 | No crystal grain | sliding portion whitened On-resistance 900 kΩ | 10.1 |
| Comparative Example 3 | 165° C. 75 min | 86.5 | 460 | 0.21 | 10 | sliding portion whitened On-resistance 900 kΩ | 10.1 |
| Comparative Example 4 | 165° C. 75 min | 88.6 | 1050 | 0 | No crystal grain | sliding portion whitened On-resistance 900 kΩ | 9.0 |
| Comparative Example 5 | 165° C. 75 min | 86.4 | 734 | 0.83 | 8 | sliding portion whitened On-resistance 900 kΩ | 10.0 |

TABLE 1-continued

| | | | | | | | |
|---|---|---|---|---|---|---|---|
| Comparative Example 6 | 165° C. 75 min | 86.9 | 350 | 34.12 | 340 | Transparent at sliding portion On-resistance 0.2 kΩ | 22.0 |
| Comparative Example 7 | 165° C. 75 min | 86.3 | 680 | 52.22 | 1100 | Transparent at sliding portion On-resistance 0.2 kΩ | 22.3 |

(*1) "Methods of controlling partial pressure of water/partial pressure of argon" [1] to [3]
[1]: Method of controlling introduction of water by a mass flow controller
[2] Method of controlling introduction of a hydrogen atom-containing gas by a mass flow controller (a hydrogen gas is used in the example)
[3]: Method of control by temperature of a center roll via a temperature controller As indicated in Table 1, the transparent conductive films in Examples 1 to 9 are excellent in pen sliding durability and flexibility, thus having both characteristics in combination. In Comparative Examples 1 to 7, however, either the pen sliding durability or the flexibility cannot be attained.

INDUSTRIAL APPLICABILITY

As described above, a transparent conductive film excellent in pen sliding durability and flexibility can be prepared according to the present invention. The transparent conductive film is very useful for application such as a resistive film type touch panel.

REFERENCE SIGNS LIST

1. Film
2. Center roll
3. Chimney
4. Indium-tin composite oxide target

The invention claimed is:

1. A transparent conductive film comprising a transparent plastic film substrate and an indium-tin composite oxide transparent conductive film laminated on at least one surface of the transparent plastic film substrate, a value of normalized integrated intensity of a diffraction peak measured by X-ray diffractometry in a (222) plane due to a crystal of the transparent conductive film being 4 to 25 cps·°/nm,
   wherein the value of normalized integrated intensity of the diffraction peak measured by X-ray diffractometry in a (222) plane due to the crystal of the transparent conductive film is obtained as follows:
   the X-ray diffractometry is performed at an incident angle of the X-ray of 0.25°, with a scintillation counter detector scanned in an out-of-plane direction, and at a step interval of 0.02° and a measurement speed of 2.0°/min;
   a diffraction peak curve in the (222) plane having a peak top at about 30.5(2θ) is obtained when the incident angle on the (222) plane is plotted as the horizontal axis and the intensity of a diffraction peak is plotted as the vertical axis;
   integrated intensity of the diffraction peak in the (222) plane is calculated as an area of the diffraction peak curve in which background subtraction is performed; and
   a value obtained by dividing the integrated intensity of the diffraction peak in the (222) plane by a thickness of the transparent conductive film is defined as the value of normalized integrated intensity of the diffraction peak measured by X-ray diffractometry in the (222) plane due to the crystal of the transparent conductive film.

2. The transparent conductive film according to claim 1, wherein the indium-tin composite oxide transparent conductive film has a crystal grain size of 10 to 1000 nm.

3. The transparent conductive film according to claim 1, wherein the indium-tin composite oxide transparent conductive film includes 0.5 to 10% by mass of tin oxide.

4. The transparent conductive film according to claim 1, wherein the indium-tin composite oxide transparent conductive film has a thickness of 10 to 30 nm.

* * * * *